(12) United States Patent
Stahmann et al.

(10) Patent No.: US 7,981,042 B2
(45) Date of Patent: Jul. 19, 2011

(54) USE OF EXTERNAL RESPIRATORY THERAPY DEVICE TO DETECT CARDIAC ELECTRICAL ACTIVITY

(75) Inventors: Jeffrey E. Stahmann, Ramsey, MN (US); Jesse W. Hartley, Lino Lakes, MN (US); Kent Lee, Shoreview, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 281 days.

(21) Appl. No.: 12/069,989

(22) Filed: Feb. 14, 2008

(65) Prior Publication Data

US 2008/0139948 A1    Jun. 12, 2008

Related U.S. Application Data

(63) Continuation of application No. 10/922,351, filed on Aug. 19, 2004, now Pat. No. 7,364,547.

(60) Provisional application No. 60/504,356, filed on Sep. 18, 2003.

(51) Int. Cl.
*A61B 5/0205* (2006.01)
(52) U.S. Cl. ......... 600/484; 600/483; 600/509; 600/529
(58) Field of Classification Search ................. 600/483, 600/484, 513, 529, 509
See application file for complete search history.

(56) References Cited

U.S. PATENT DOCUMENTS

| | | | |
|---|---|---|---|
| 4,875,477 A | 10/1989 | Waschke et al. | |
| 5,353,788 A | 10/1994 | Miles | |
| 5,590,648 A | 1/1997 | Mitchell et al. | |
| 5,626,151 A | 5/1997 | Linden | |
| 5,974,340 A | 10/1999 | Kadhiresan | |
| 6,120,441 A | 9/2000 | Griebel | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,351,669 B1 | 2/2002 | Hartley et al. | |
| 6,353,759 B1 | 3/2002 | Hartley et al. | |
| 6,358,203 B2 | 3/2002 | Bardy | |

(Continued)

FOREIGN PATENT DOCUMENTS

WO    WO 99/04841    4/1999

(Continued)

OTHER PUBLICATIONS

2006, Office Action from U.S. Appl. No. 10/922,351 dated May 3, 2006, 11 pages.

(Continued)

*Primary Examiner* — Carl H Layno
*Assistant Examiner* — Paula J Stice
(74) *Attorney, Agent, or Firm* — Hollingsworth & Funk, LLC

(57) ABSTRACT

Methods and systems provide an integrated approach to respiratory and cardiac monitoring, diagnosis and/or therapy. A medical system includes one or more cardiac electrodes coupled to an external respiratory therapy device. The cardiac electrodes sense cardiac electrical activity that is used to generate an electrocardiogram (ECG) signal. Cardiac events, such as arrhythmia, myocardial infarction and/or ischemia, may be detected based on the sensed cardiac electrical activity.

18 Claims, 11 Drawing Sheets

U.S. PATENT DOCUMENTS

| | | |
|---|---|---|
| 6,363,270 B1 | 3/2002 | Colla et al. |
| 6,368,284 B1 | 4/2002 | Bardy |
| 6,397,845 B1 | 6/2002 | Burton |
| 6,398,728 B1 | 6/2002 | Bardy |
| 6,411,848 B2 | 6/2002 | Kramer et al. |
| 6,440,066 B1 | 8/2002 | Bardy |
| 6,606,993 B1 | 8/2003 | Wiesmann et al. |
| 6,752,765 B1 * | 6/2004 | Strobel et al. .................. 600/536 |
| 7,204,250 B1 * | 4/2007 | Burton ..................... 128/205.23 |
| 2002/0169384 A1 * | 11/2002 | Kowallik et al. .............. 600/529 |
| 2002/0193697 A1 * | 12/2002 | Cho et al. ...................... 600/529 |
| 2003/0023184 A1 | 1/2003 | Pitts-Crick et al. |
| 2003/0100925 A1 | 5/2003 | Pape et al. |
| 2004/0035423 A1 * | 2/2004 | Platt et al. ................. 128/204.23 |
| 2004/0138719 A1 * | 7/2004 | Cho et al. ......................... 607/42 |

FOREIGN PATENT DOCUMENTS

| | | |
|---|---|---|
| WO | WO 01/43804 | 6/2001 |
| WO | WO 02/087696 | 11/2002 |

OTHER PUBLICATIONS

2006, Office Action from U.S. Appl. No. 10/922,351 dated Oct. 13, 2006, 12 pages.

2007, Office Action U.S. Appl. No. 10/922,351 dated Apr. 20, 2007, 6 pages.

* cited by examiner

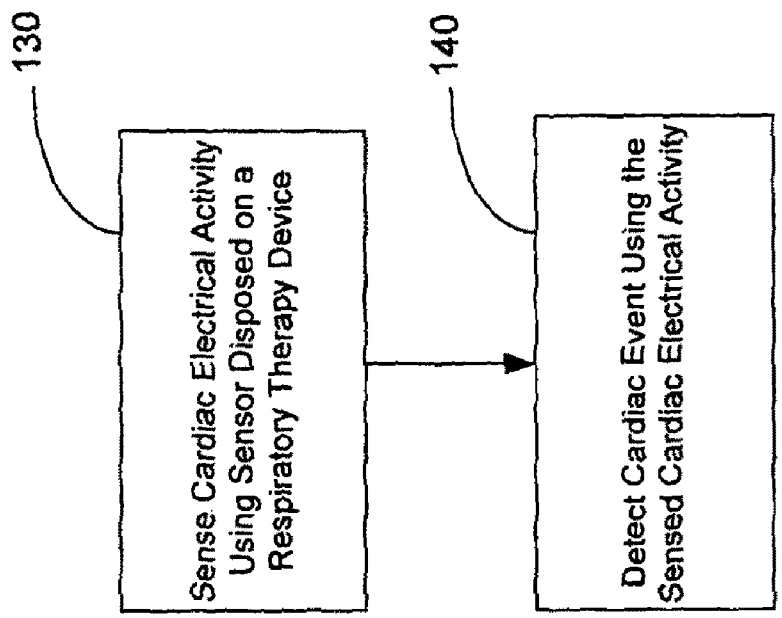
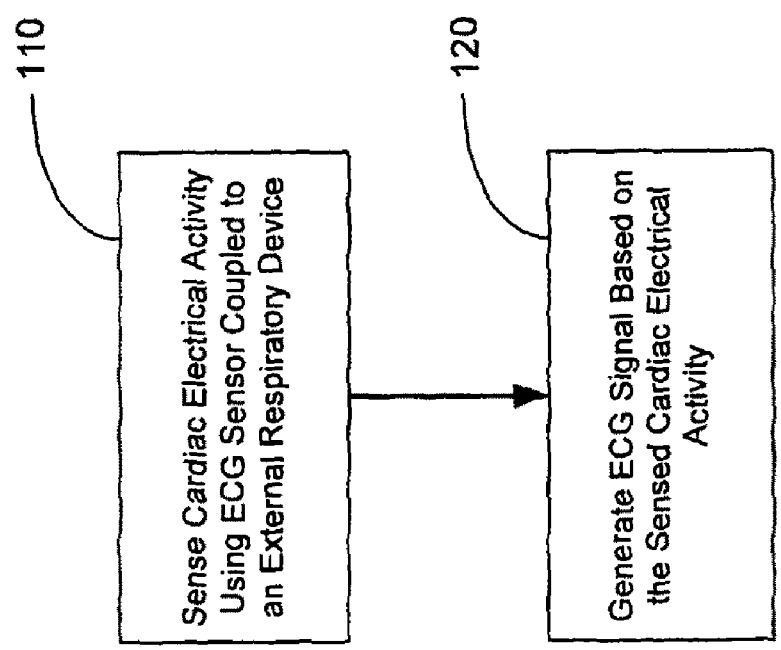
Figure 1B
Figure 1A

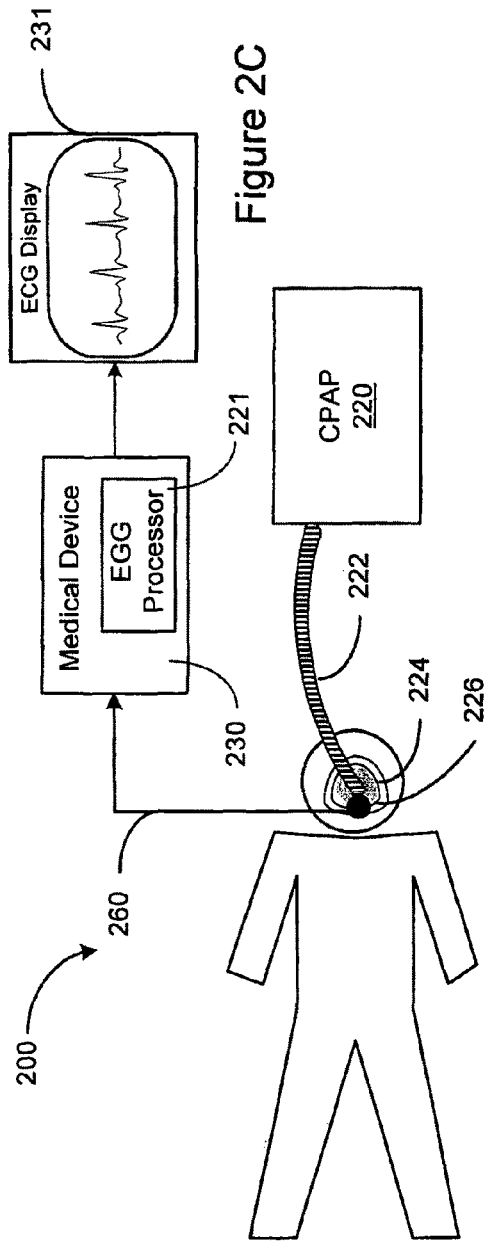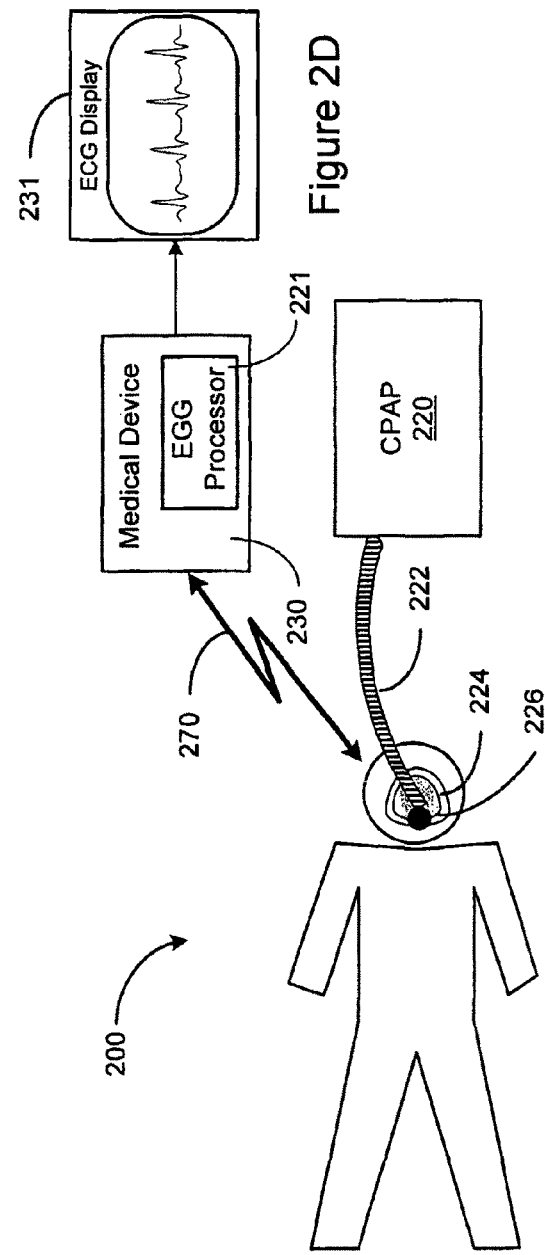

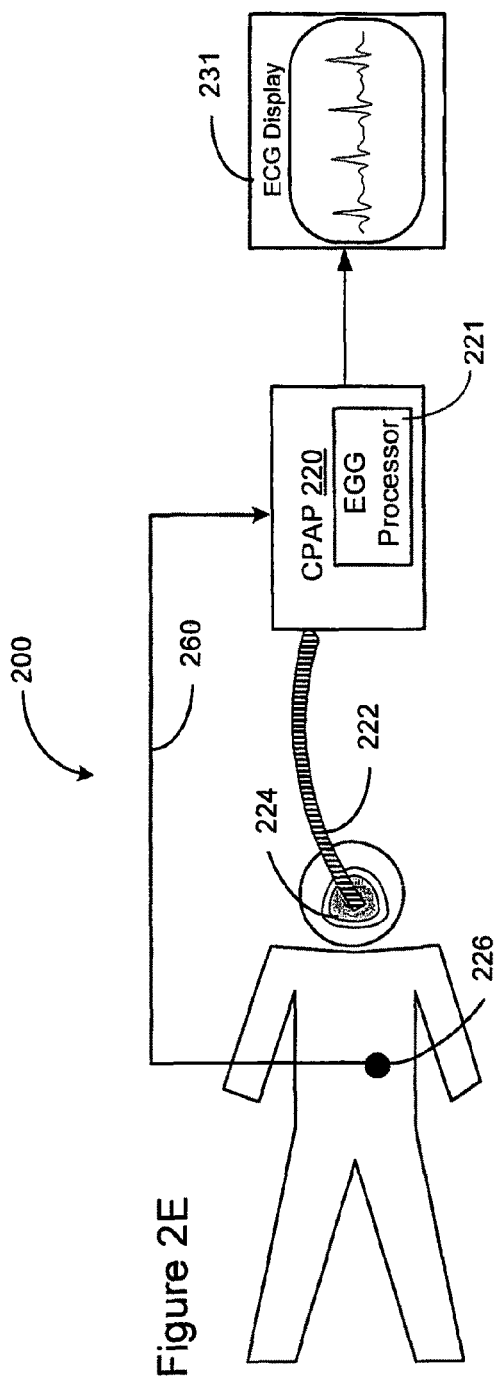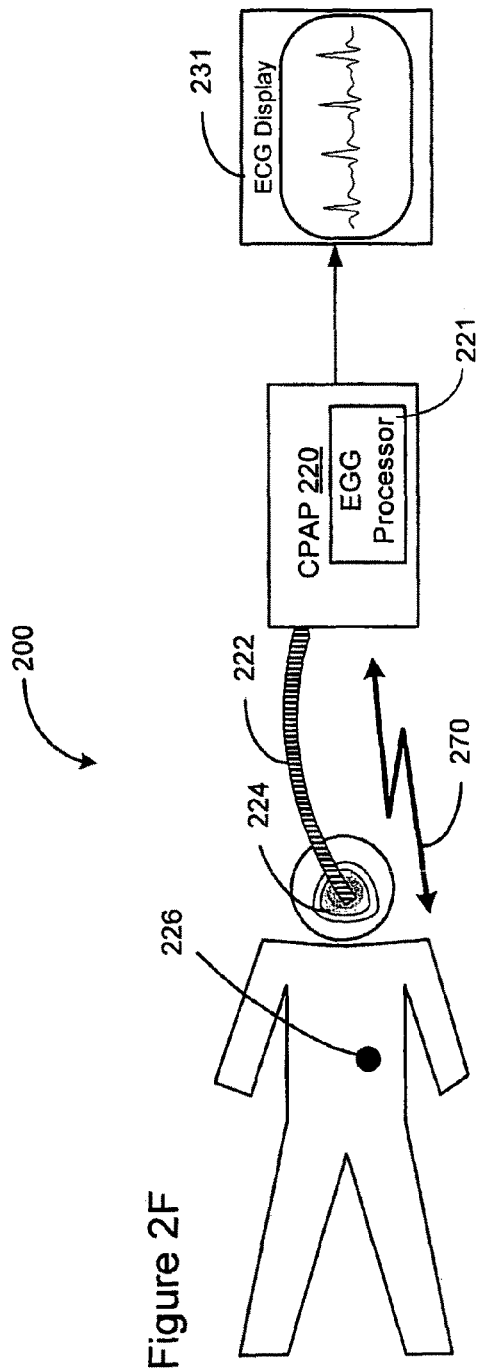
Figure 2E
Figure 2F

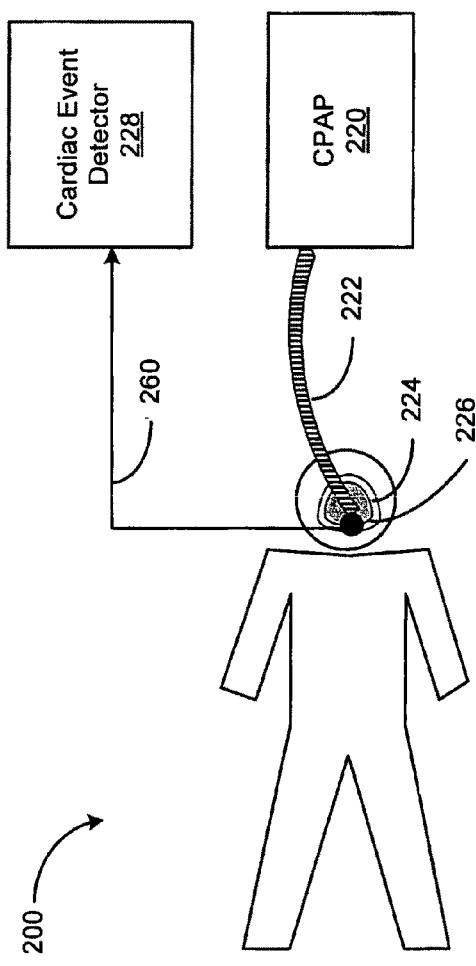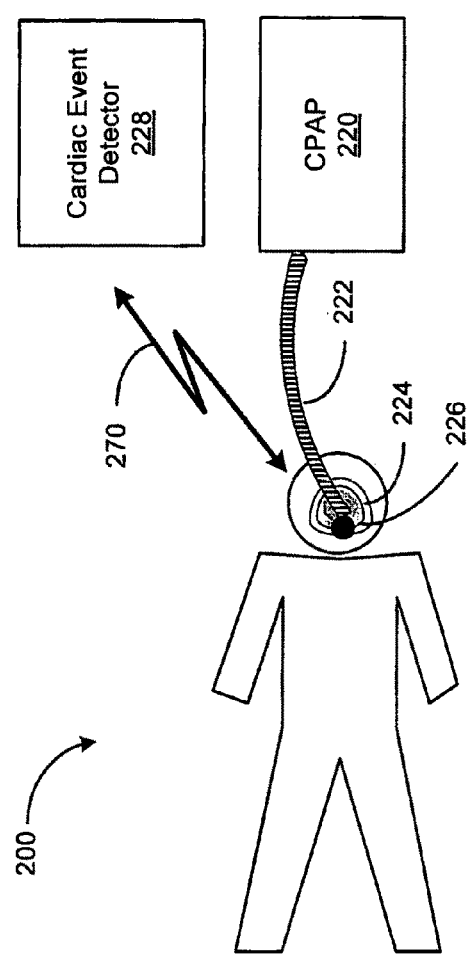

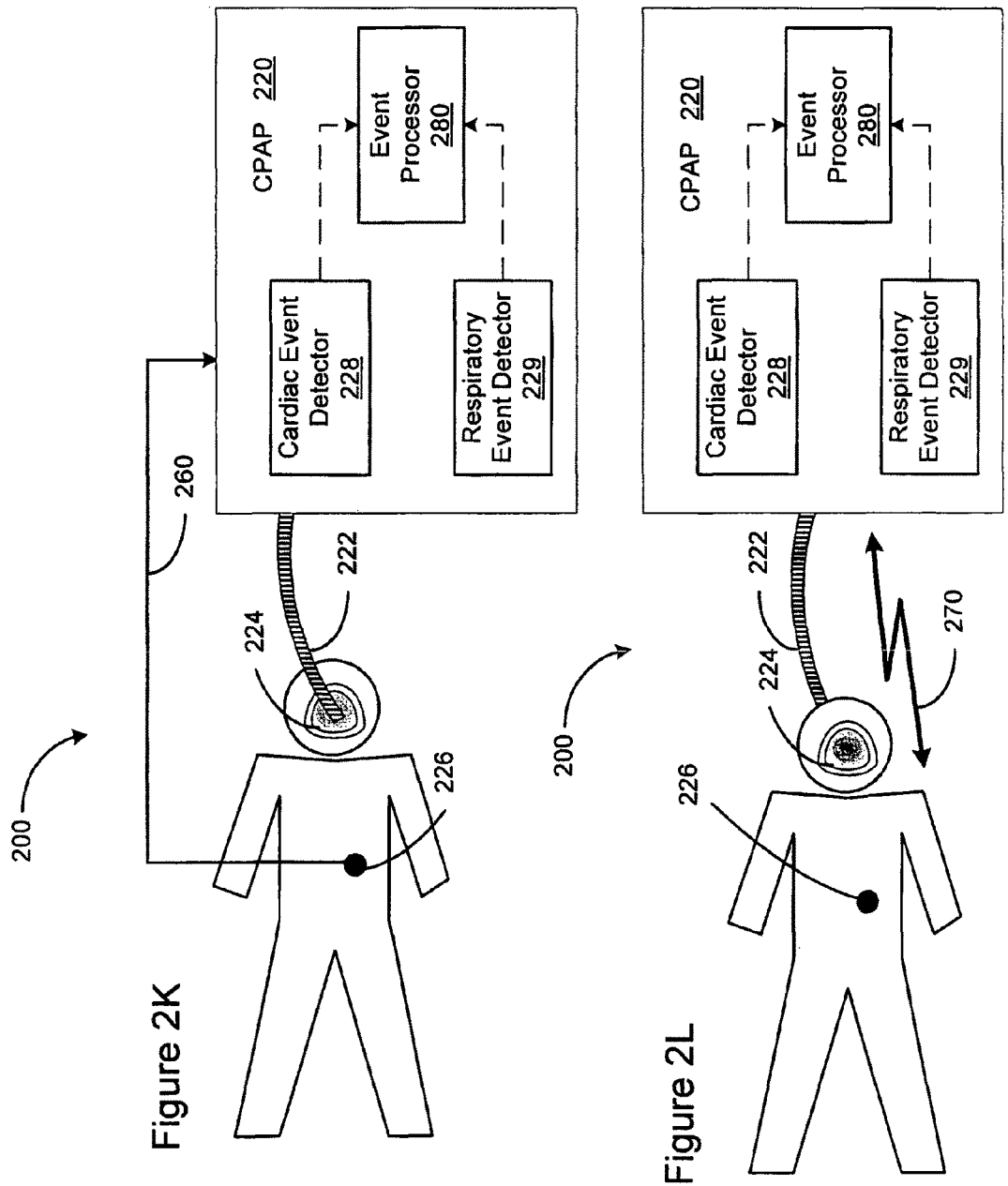

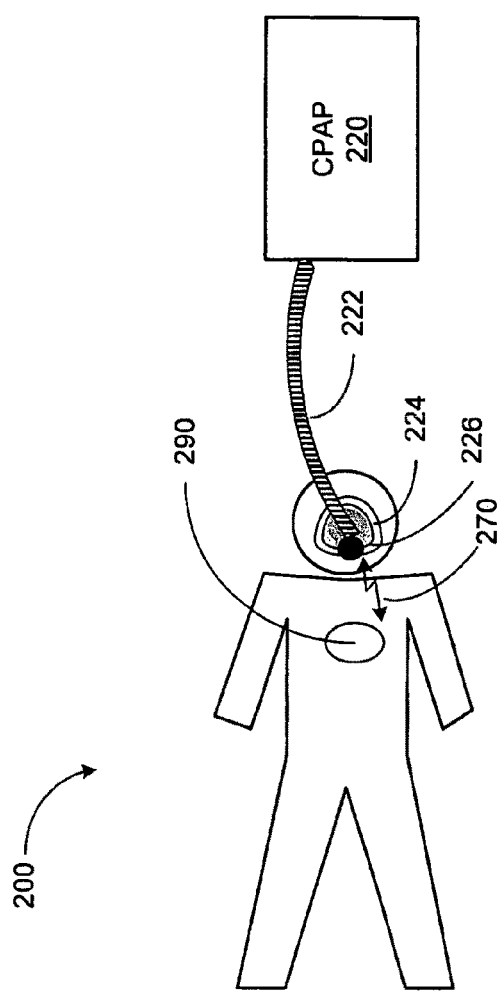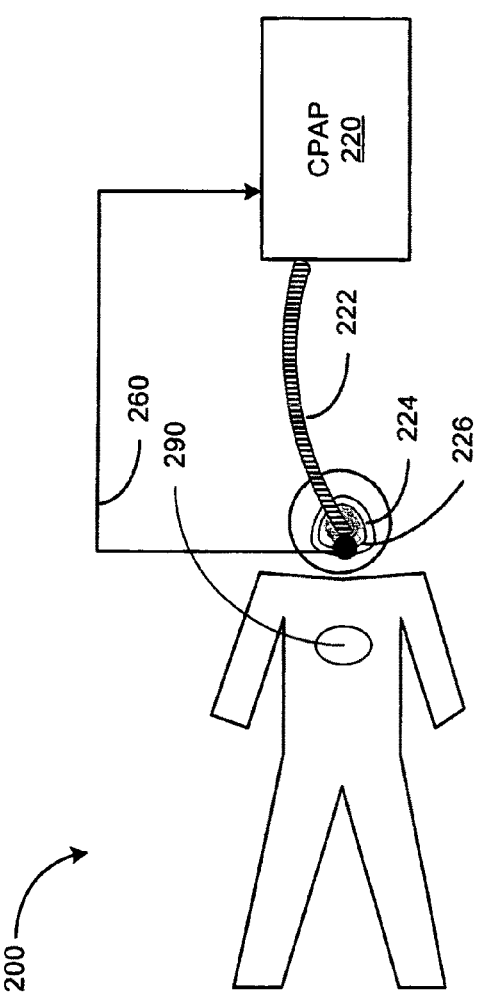

USE OF EXTERNAL RESPIRATORY THERAPY DEVICE TO DETECT CARDIAC ELECTRICAL ACTIVITY

RELATED APPLICATIONS

This application is a continuation of U.S. patent application Ser. No. 10/922,351, filed on Aug. 19, 2004, now U.S. Pat. No. 7,364,547 which claims the benefit of Provisional Patent Application Ser. No. 60/504,356, filed on Sep. 18, 2003, to which Applicant claims priority under 35 U.S.C. §120 and 35 U.S.C. §119(e), respectively, and which are incorporated herein by reference in their entireties.

FIELD OF THE INVENTION

The present invention relates generally to methods and systems for detecting cardiac electrical activity using electrodes coupled to an external respiratory therapy device.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Abnormal breathing patterns often occur in conjunction with congestive heart failure (CHF). A form of disordered breathing is known as periodic breathing (PB). In particular, a form of periodic breathing known as Cheyne-Stokes respiration (CSR) is commonly associated with poor prognosis when diagnosing CHF patients. Some studies have suggested that disordered breathing is related to a higher incidence of cardiac arrhythmia.

External breathing therapy may be prescribed for patients suffering from various types of breathing dysfunction. For example, positive airway pressure devices are often used to treat disordered breathing such as CSR and other types of disordered breathing. The positive airway pressure provided by the device acts as a pneumatic splint keeping the patient's airway open and reducing the severity and/or number of occurrences of disordered breathing events due to airway obstruction.

Effective approaches to monitoring and evaluating cardiac conditions in patients receiving therapy for respiratory disorders is desirable. The present invention fulfills these and other needs, and addresses other deficiencies of prior art implementations and techniques.

SUMMARY OF THE INVENTION

Various embodiments are directed to methods and systems for detecting cardiac electrical activity using an external respiratory therapy device. In accordance with one embodiment, a medical system includes one or more cardiac electrodes configured to sense cardiac electrical activity. The cardiac electrodes are coupled to an external respiratory therapy device. The cardiac electrical activity is used to generate an electrocardiogram (ECG) signal.

In accordance with another embodiment of the invention, a system includes sensors coupled to an external respiratory therapy device. The sensors are configured to sense electrical activity of a heart. A cardiac event detector is coupled to the one or more sensors and is configured to detect one or more cardiac events based on the sensed cardiac electrical activity.

Another embodiment of the invention involves a method for generating an electrocardiogram (ECG) signal. Cardiac electrical activity is sensed using one or more cardiac electrodes coupled to an external respiratory therapy device. The ECG signal is generated based on the sensed cardiac electrical activity.

A further embodiment involves detecting cardiac events. The method includes sensing cardiac electrical activity using one or more cardiac electrodes coupled to an external respiratory therapy device. The cardiac events are detected based on the sensed cardiac electrical activity.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1A and 1B are flowcharts of methods involving the use of electrodes coupled to an external respiratory therapy device in accordance with embodiments of the invention;

FIGS. 2A-2D are block diagrams of external respiratory therapy devices having one or more electrodes mechanically coupled to the respiratory therapy mask assembly and used in connection with generating electrocardiogram (ECG) signals in accordance with embodiments of the invention;

FIGS. 2E-2F are block diagrams of external respiratory therapy devices having one or more electrodes communicatively coupled to the respiratory therapy device controller and used in connection with generating ECG signals in accordance with embodiments of the invention;

FIGS. 2G-2J are block diagrams of external respiratory therapy devices having one or more electrodes mechanically coupled to the respiratory therapy mask assembly and used in connection with detecting cardiac events in accordance with embodiments of the invention;

FIGS. 2K-2L are block diagrams of external respiratory therapy devices having one or more electrodes communicatively coupled to the respiratory therapy device controller and used in connection with detection of cardiac events in accordance with embodiments of the invention;

FIGS. 2M-2N are block diagrams of an external respiratory therapy device having cardiac electrodes communicatively coupled to an implantable medical device in accordance with embodiments of the invention;

Figure 2A:
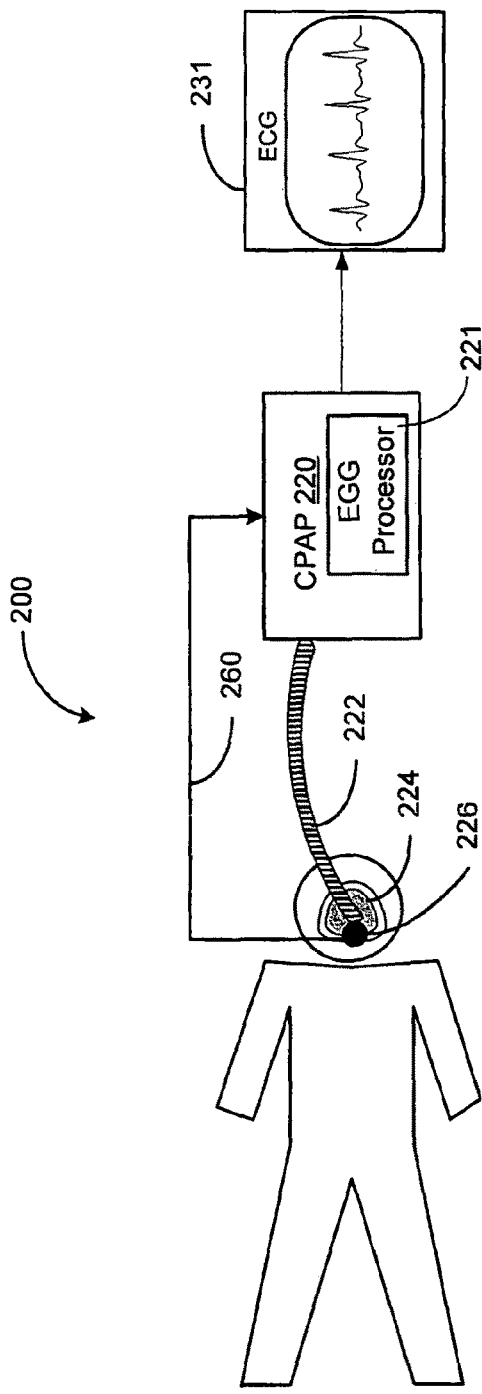
Figure 2B:
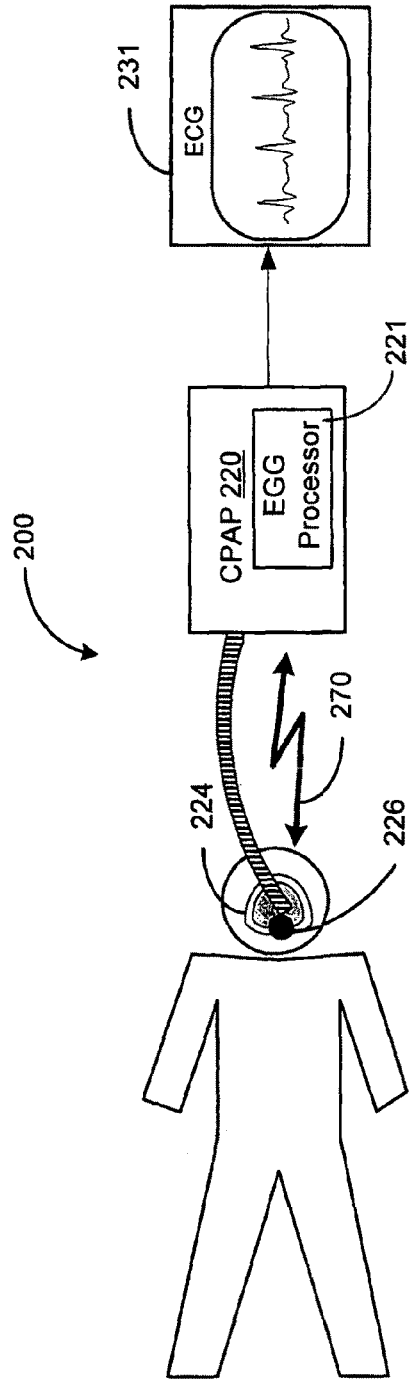
Figure 2G:
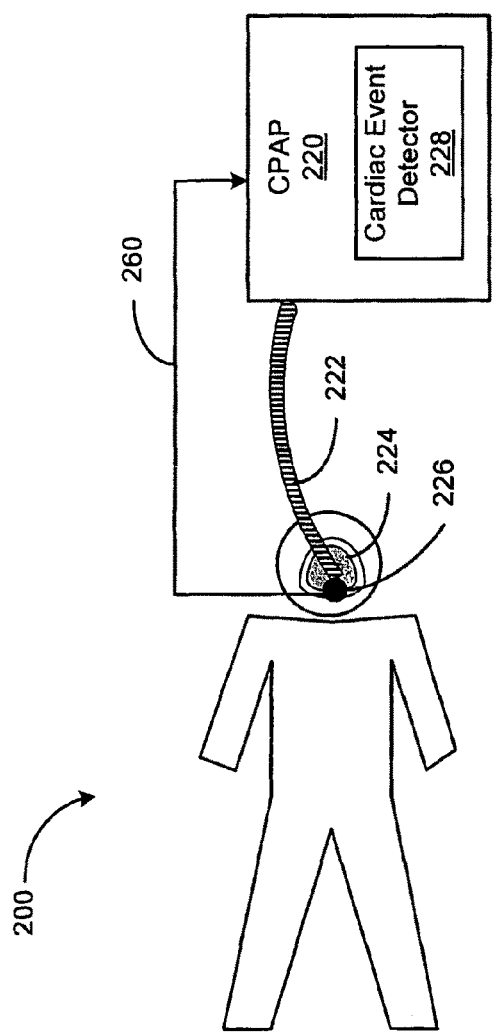
Figure 2H:
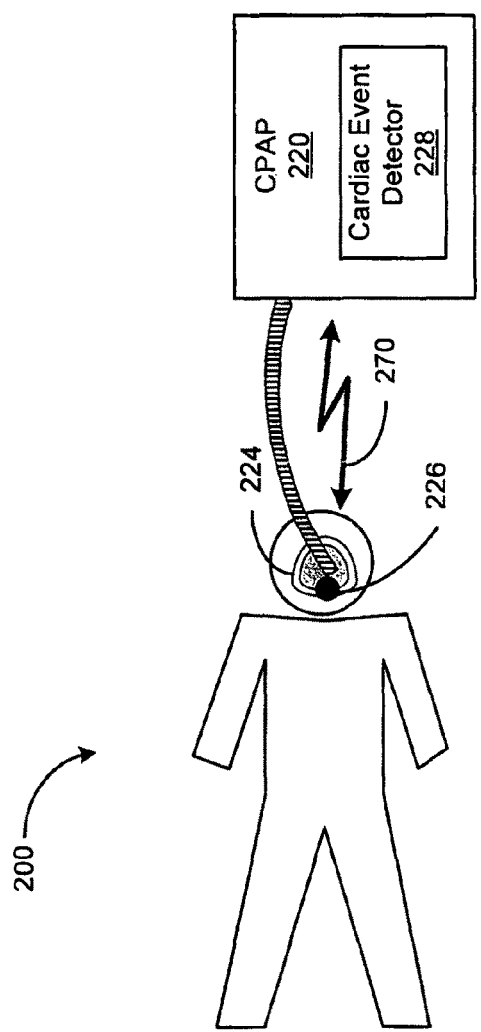

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Treatment of respiratory disorders may involve the use of an external respiratory therapy device. Respiratory therapy devices may include a respiratory mask assembly that fits over the patient's nose and/or face and directs a flow of gas to the patient. The mask assembly is connected through a tube to a control unit that controls the flow of air or other gas to the patient. Sensors on the mask, in the control unit, or elsewhere may facilitate control of the respiratory therapy delivered to the patient.

External respiratory therapy devices are often used to treat breathing disorders, such as sleep disordered breathing. Sleep apnea is a common form of sleep disordered breathing and is characterized by periods of interrupted breathing during sleep. Apnea and other types of disordered breathing may be caused blockage of the airway due to prolapse of soft tissue into the throat (obstructive apnea) and/or by derangement of the central nervous system signals controlling the breathing reflex. The cessation of breathing may occur repeatedly during sleep, sometimes hundreds of times a night and sometimes for a minute or longer. Respiratory therapy for sleep disordered breathing typically involves the use of an external respiratory device during the night. The external respiratory therapy device delivers positive airway pressure to the patient. The positive air pressure acts as a pneumatic splint, keeping the patient's airway open and reducing episodes of disordered breathing.

Patient's suffering from respiratory disorders may concurrently experience cardiac dysfunction. Sleep apnea and cardiac arrhythmia are common comorbidities. Further, Cheyne-Stokes respiration is frequently observed in patients with congestive heart failure. Cheyne-Stokes respiration in congestive heart failure patients is associated with poor prognosis and may be used to track the progression of the disease. Cardiac arrhythmias have been associated with the hypoxia or autonomic arousal from sleep disordered breathing.

Although cardiac conditions and respiratory disorders are commonly found in combination, monitoring and/or treatment of the disorders is generally accomplished using separate medical devices. Respiratory disorders such as disordered breathing have traditionally been treated using the above-described external respiratory therapy devices. Monitoring cardiac conditions such as cardiac arrhythmia may be accomplished using a patient worn or carried monitor, for example, a Holter monitor, having electrodes attached to the patient's chest for detecting cardiac electrical activity. Cardiac conditions such as arrhythmia and congestive heart failure may also be monitored and/or treated using an implantable cardiac rhythm management (CRM) system.

The nightly use of an external respiratory therapy device by the patient provides an opportunity to detect and/or diagnose cardiac disorders in addition to respiration disorders. Embodiments of the invention involve the use of cardiac sensors used in cooperation with a respiratory therapy device. The cardiac sensors sense cardiac electrical activity used to generate an electrocardiogram signal. Further embodiments of the invention involve detecting cardiac arrhythmia based on the sensed cardiac electrical activity.

FIGS. 1A and 1B are flowcharts illustrating methods of using a cardiac electrical activity sensor disposed on a respiratory therapy device in accordance with embodiments of the invention. One or more electrodes are disposed 110, 130 on a respiratory therapy device in locations that facilitate sensing cardiac electrical activity. The electrodes may be positioned on a respiratory mask, mask strap, or in other locations of the respiratory therapy device from which cardiac signals can be sensed. In one embodiment, the sensed cardiac electrical activity is used 120 to generate an electrocardiogram (ECG) signal. In another embodiment, the sensed cardiac electrical activity signal is used 140 to detect arrhythmia.

FIGS. 2A-2F illustrate various embodiments for sensing cardiac activity and generating ECG signals using electrodes coupled to an external respiratory therapy device. In some embodiments, cardiac electrodes disposed on the mask of an external respiratory device sense cardiac signals. Circuitry coupled to the electrodes generates an ECG waveform. The ECG waveform generating circuitry coupled to the electrodes may be disposed on the mask, within the CPAP controller, or in another location.

In the illustrative examples presented herein, the external respiratory therapy device is configured as a continuous positive airway pressure (CPAP) device 220 including a controller 220, tubing 222, and respiratory mask apparatus 224. Any type of external respiratory therapy device other than CPAP can alternatively be used, such as bi-level positive airway pressure devices, auto titrating positive airway pressure devices, nebulizers, respirators, ventilators, and other external respiratory therapy devices. The CPAP controller 220 develops a positive air pressure that is delivered to the patient's airway through tubing 222 and mask assembly 224. The positive airway pressure provided by the respiratory therapy device 200 acts as a pneumatic splint keeping the patient's airway open and reducing the severity and/or number of occurrences of disordered breathing due to airway obstruction.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term CPAP will be used herein as a generic term for any device using forms of positive airway pressure (and negative pressure when necessary), whether continuous or otherwise.

In some embodiments (FIGS. 2A-2D), the one or more cardiac electrodes 226 are mechanically coupled to the respiratory therapy device 200. The electrodes 226 may be positioned on the mask assembly 224 of the external respiratory device 200. For example, electrodes 226 may be positioned on the mask, mask strap, or other appropriate location on the mask assembly in a location that facilitates sensing cardiac electrical activity. The mask assembly 224 serves to hold the electrodes 226 in place while the external respiration therapy is delivered to the patient.

In some configurations, the electrodes 226 are coupled to an ECG processor 221 that uses the cardiac signals sensed by the electrodes 226 to generate an ECG waveform. The ECG processor 221 may be disposed, for example, within or on the CPAP controller unit. The electrodes 226 may be coupled to the ECG processor 221 through a wire lead 260.

In some implementations, the ECG processor 221 may be positioned proximate the electrodes 226, for example, on the respiratory mask assembly. This configuration facilitates generation of an ECG waveform that may be transmitted via a wireless communications link 270 to the CPAP controller 220 or other medical devices 230.

The ECG waveform generated by the ECG processor 221 may be printed on a printing device, displayed on a display device 231, stored in memory, and/or analyzed by circuitry disposed within the CPAP controller 220 and/or the cooperating medical device 230.

If the patient uses the external respiratory therapy device regularly, for example each night, data acquisition via the electrodes 226 coupled to the external respiratory device 200 allows a significant amount of information about the patient's cardiac functioning to be collected during each sleep period. In some implementations, the cooperating medical device 230 may comprise a patient-worn or patient-carried device. In other implementations, the medical device 230 may comprise an implantable device, for example, an implantable monitor or implantable therapy device.

In some embodiments (FIGS. 2C and 2D), the ECG processor 221 may be disposed within the medical device 230. The medical device 230 may additionally include circuitry for storing and/or analyzing the ECG signals. Information about the ECG signals may be downloaded from the medical device 230 to an external device for display, analysis, or storage, for example.

In one configuration, the electrodes 226 may be communicatively coupled to the external device 230 through a wire lead 260. In another configuration, additional circuitry, e.g., amplifiers and/or transmitter circuitry, may be used to provide a wireless link 270 between the cardiac electrodes 226 and the device 230.

In some embodiments (FIGS. 2E and 2F), one or more cardiac electrodes 226 may be positioned on the patient's chest, or another location suitable for sensing cardiac electrical activity. The cardiac electrodes may be communicatively coupled to the external respiratory device 200. For example, the sensors may be communicatively coupled to the CPAP controller 220 through a wire lead 260 (FIG. 2E). Alternatively, additional circuitry may be situated proximate the electrodes to facilitate communication with the CPAP controller 220 through a wireless communications link 270 (FIG. 2F).

FIGS. 2G-2L illustrate embodiments of the invention involving cardiac event detection using one or more cardiac electrodes 226 coupled to an external respiratory therapy device 200. In some embodiments (FIGS. 2G-2J), the electrodes 226 are mechanically coupled to the respiratory mask apparatus 224. The respiratory mask apparatus 224 serves as a support for the electrodes 226 positioning the electrodes against the patient's face to facilitate sensing cardiac electrical activity. The electrodes 226 are coupled to an external or implantable cardiac event detector 228 through wired 260 or wireless 270 connections. In some embodiments (FIGS. 2G and 2H), the cardiac event detector 228 is disposed within or on the CPAP controller 220 housing. In other embodiments (FIGS. 2I and 2J), cardiac event detector 228 circuitry is separate from the CPAP controller 220.

FIGS. 2K and 2L illustrate embodiments of the invention wherein one or more cardiac electrodes 226 are positioned on the patient's chest or other location suitable for sensing cardiac electrical activity. The electrodes are coupled to a cardiac event detector 228 of an external respiratory therapy device 200. The electrodes 226 may be coupled to the cardiac event detector 228 through a wire lead 260 or through a wireless connection 270.

The CPAP device 220 may optionally include a respiratory event detector 229. In accordance with one implementation, the respiratory event detector may be used to provide feedback for therapy control. For example, CPAP therapy may be initiated or adjusted based on the presence, absence, severity, frequency and/or duration of disordered breathing events detected by the respiratory event detector.

If a respiratory event detector is included, the respiratory event detector and the cardiac event detector may be coupled to an event processor 280. The event processor 280 may be used to detect physiological events, including events affecting one or more of the cardiac and pulmonary systems based on inputs from the cardiac and respiratory event detectors. The cardiac event detector, respiratory event detector and/or event processor may be employed to detect various cardiac and/or respiratory dysfunctions, including, for example, bradycardia, tachycardia, including atrial tachyarrhythmia, ventricular tachyarrhythmia and ventricular fibrillation, myocardial ischemia, and/or myocardial infarction. The event processor may compare occurrences of respiratory and cardiac events including one or more of the timing, severity, type, and occurrence rate of the respiratory and cardiac events and detect the physiological events based on these and/or other factors.

The cardiac event detection circuitry illustrated, for example, in FIGS. 2I and 2J may be implemented in a patient carried or patient worn device, or in an implantable device such as a cardiac defibrillator or pacemaker.

FIG. 2M illustrates an embodiment of the invention wherein one or more cardiac electrodes 226, and circuitry used to establish a wireless communications link 270, are disposed on the CPAP mask assembly 224. In FIG. 2M, signals sensed by the cardiac electrodes are transmitted to an implantable device 290, bypassing the CPAP controller 220.

The implantable device 290 may comprise, for example, an implantable therapy device, such as an implantable electrical stimulation device or implantable drug pump. The implantable device may comprise an implantable monitor. In one implementation, the implantable device 290 may comprise an implantable pacemaker, defibrillator, cardioverter, cardiac resynchronizer, or other cardiac therapy devices that receives the ECG signals. In another implementation, the implantable device 290 may comprise an implantable loop recorder, such as a subcutaneous ECG recorder. The implantable device may include a cardiac event detector that analyzes the ECG signals to detect cardiac events including cardiac arrhythmia, ischemia, and/or myocardial infarction.

FIG. 2N illustrates an embodiment wherein the cardiac electrodes 226 are coupled to the CPAP device 220 through a wire lead. Signals received by the CPAP device 220 may be wirelessly transmitted to the implantable device 290 for storage, analysis or for other purposes.

Figure 3A:
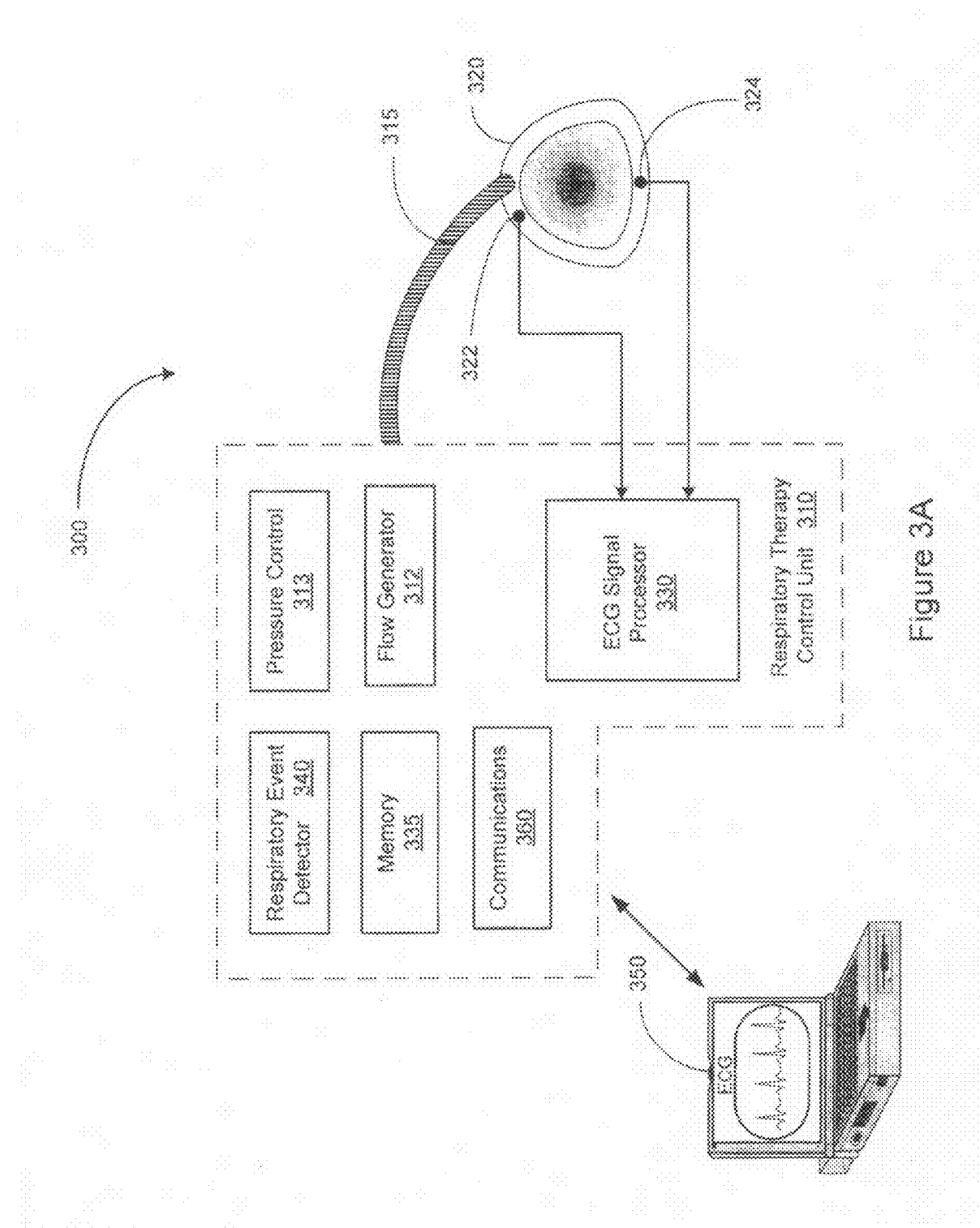
FIG. 3A is a block diagram of an external respiratory therapy device including one or more electrodes mechanically coupled to the respiratory therapy mask assembly and a respiratory therapy controller incorporating an ECG signal processor in accordance with embodiments of the invention.
Figure 3B:
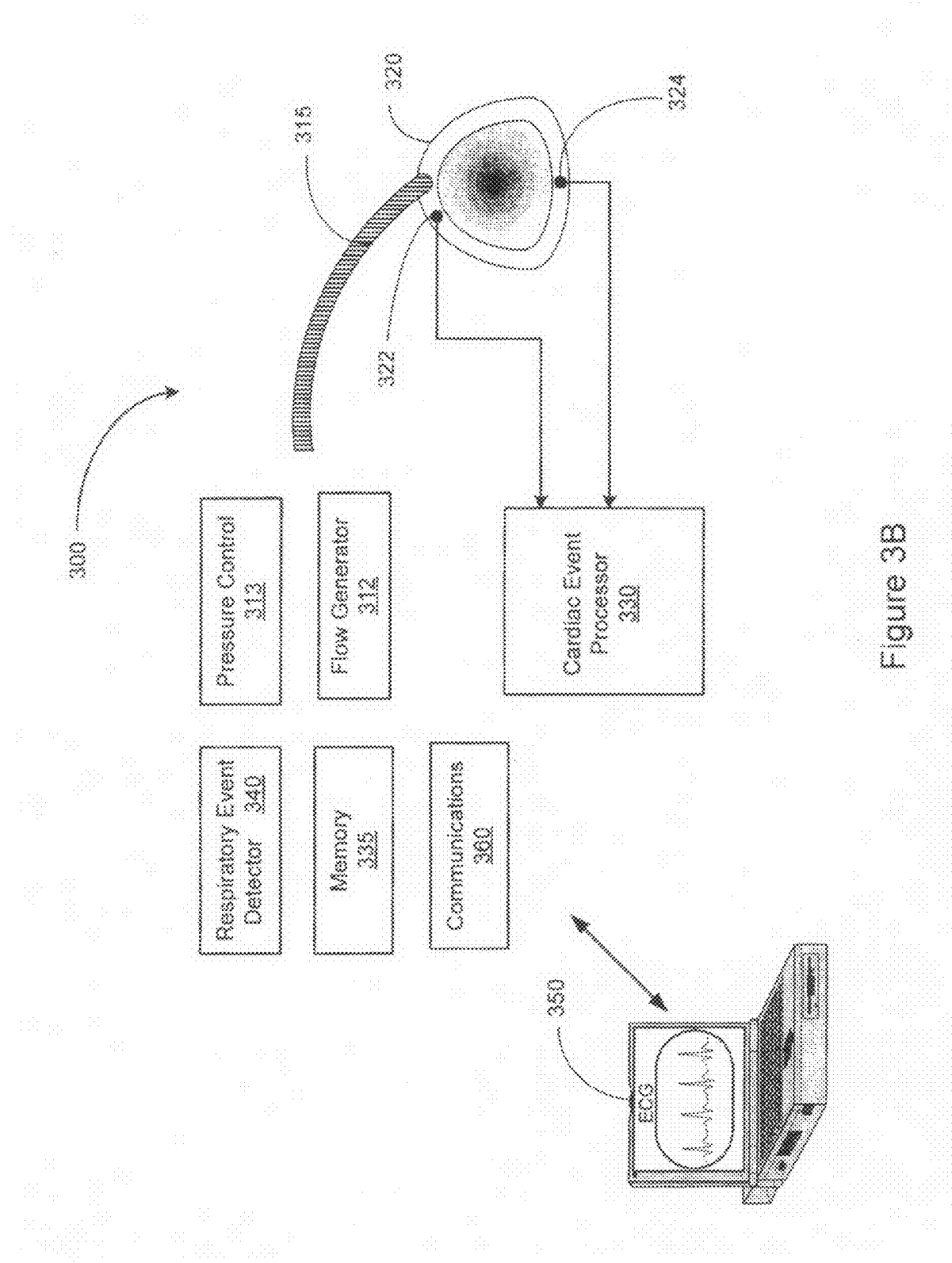
FIG. 3B is a block diagram of an external respiratory therapy device including one or more electrodes mechanically coupled to the respiratory therapy mask assembly and a respiratory therapy controller incorporating cardiac event detector in accordance with embodiments of the invention.

FIGS. 3A and 3B are block diagrams of a medical system including an external respiratory therapy device that may be used in connection with sensing cardiac electrical activity. FIG. 3A illustrates an embodiment that directed to generating an electrocardiogram signal in accordance embodiments of the invention. FIG. 3B illustrates an embodiment that uses the sensed electrical cardiac activity to detect arrhythmia.

FIGS. 3A and 3B depict block diagrams of a CPAP device 300 having cardiac sensing capabilities in accordance with the present invention. The CPAP device includes a CPAP controller 310, tubing 315, and mask assembly 320. The CPAP controller unit may include a respiratory event detector 340 configured to detect disordered breathing episodes, such as sleep apnea and/or hypopnea. Detection of disordered breathing may be used to initiate or adjust respiratory therapy delivered to the patient.

The CPAP controller unit 310 includes flow generator 312 that pulls in air through a filter. The flow generator 312 is controlled by the pressure control circuitry 313 to deliver an appropriate air pressure to the patient. Air flows through tubing 315 coupled to the CPAP device 310 and is delivered to the patient's airway through the mask assembly 320. The CPAP controller 310 may be coupled through communications circuitry 360 to other computing devices 350, such as a programmer or patient management server to facilitate storage, evaluation and/or display of the cardiac information.

In embodiments of the present invention, the mask apparatus 320 may comprise a nasal mask covering only the patient's nose. In other configurations the mask covers the patient's nose and mouth. One or more cardiac electrodes may be coupled to the CPAP device 300. For example, the one or more cardiac electrodes 322, 324 may be incorporated on the respiratory therapy mask 320. However, the one or more cardiac electrodes 322, 324 can be positioned in another location of the respiratory therapy device that facilitates acquisition of a cardiac signal. For example, electrodes 322 can be incorporated in a respiratory mask strap (not shown).

As illustrated in FIG. 3A, the cardiac electrodes 322, 324 are communicatively coupled to signal processing circuitry 330 within the CPAP controller 310. The cardiac activity information is used to generate an electrocardiogram signal. The ECG signal can be used by the CPAP control unit 310 to control the external respiratory therapy delivered to the patient. Additionally or alternatively, the ECG signal can be stored in memory 335, used to generate an ECG display or printout, and/or evaluated for diagnostic or therapeutic purposes.

FIG. 3B illustrates a block diagram of an embodiment of the invention that involves detection of cardiac arrhythmia. In this configuration, cardiac electrodes 322, 324 positioned on the respiratory mask 320, sense cardiac electrical activity. The electrodes 322, 324 are coupled to an arrhythmia detector 360 disposed within a housing of the respiratory therapy control unit 310. The cardiac event detector 360 uses the cardiac electrical activity sensed by the electrodes 322, 324 to detect cardiac events, such as bradycardia, ventricular tachyarrhythmia, ventricular fibrillation, and/or other arrhythmic events. In one implementation, the cardiac event detector 360 may evaluate the cardiac electrical activity to determine heart rate and detect arrhythmia based on heart rate. In another implementation, the arrhythmia detector 360 may analyze the morphology of the cardiac electrical activity signal and detect arrhythmia based on the morphology of the cardiac electrical activity signal. Other methods of arrhythmia detection are possible.

Figure 4:
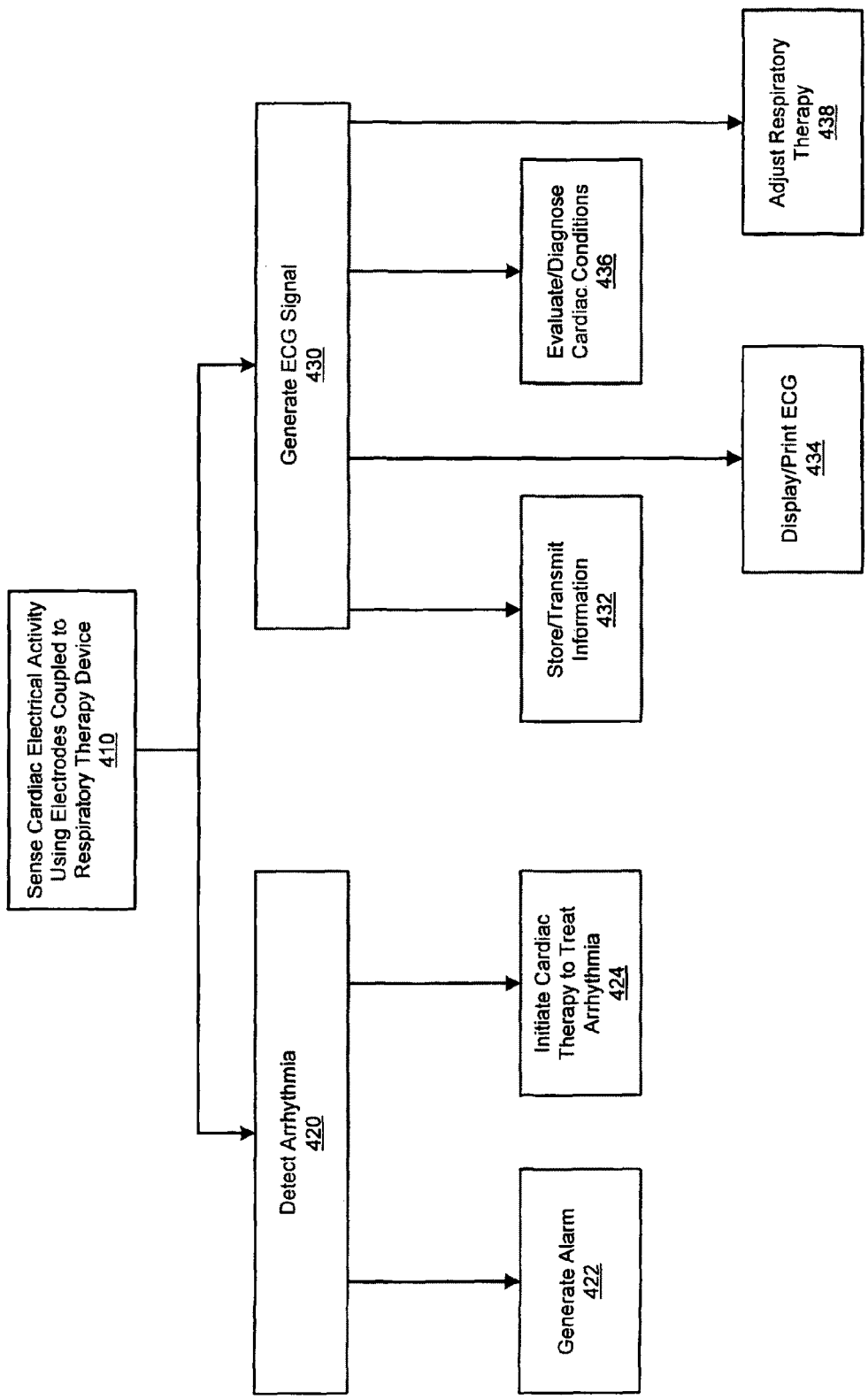
FIG. 4 is a process flow diagram illustrating various optional processes that may be implemented using one or more electrodes coupled to an external respiratory therapy device.

FIG. 4 illustrates various optional processes that may be facilitated using cardiac electrodes coupled to a respiratory therapy device. Cardiac electrical activity is sensed using electrodes coupled to an external respiratory therapy device 410. According to one aspect of the invention, the sensed cardiac activity may be used to detect arrhythmia 420. If arrhythmia is detected, an alarm may be generated 422, such as an audible or visual alarm. The alarm may include various tones or signals to indicate more than one type of arrhythmic condition, for example. In one implementation, the alarm may involve wireless communication with a remote device, such as a cell phone or pager, for example.

The sensed cardiac activity may be used to generate 430 an ECG signal. The ECG signal may be stored and/or transmitted 432 to a separate device. For example, the ECG signal may be transmitted to a patient management server for further analysis. The ECG waveform may be displayed 434 on a display device or printed. The ECG signal may be used to initiate cardiac therapy 424 to treat an arrhythmia.

Detected cardiac events and detected respiratory events may also be analyzed to determine relationships between cardiac and respiratory events. The results of this comparison may be displayed, stored, transmitted or used to modify cardiac or respiratory therapy.

Acquisition of ECG signals over a period of time may be used to trend cardiac conditions and/or diagnose 436 cardiac dysfunction, for example. Further, the ECG signals may be evaluated may be used to adjust 438 the patient's therapy, such as the external respiratory therapy delivered to the patient.

The ECG signal may be analyzed to detect morphological characteristics and/or cardiac timing measurements indicative of heart status including, for example, RR interval, PP interval, AV interval, PR interval, QT interval and/or ST elevation. The ECG signal may be used to determine statistics derived from heart rates, such as heart rate variability and various cardiac timing measurements, including RR timings and AV delay timing. Various cardiac events and/or other indications of heart status may be determined based on the ECG signal, including arrhythmia, myocardial ischemia, and/or other events. These analyses may be used to identify patient's cardiac condition and adjust therapy.

A number of the examples presented herein involve block diagrams illustrating functional blocks used for in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Methods, devices, and systems in accordance with the present invention may incorporate one or more of the features, structures, methods, or combinations thereof described herein below. For example, a medical system may be implemented to include one or more of the features and/or processes described below. It is intended that such a method, device, or system need not include all of the features and functions described herein, but may be implemented to include one or more selected features and functions that provide unique structures and/or functionality.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical system, comprising:
   an external respiratory therapy device configured to deliver an external respiratory therapy to a patient, the external respiratory therapy device including:
      a respiratory event detector configured to detect respiratory events;
      control circuitry configured to adjust the respiratory therapy based on the detected respiratory events;
      one or more cardiac electrodes configured to sense cardiac electrical activity, the one or more cardiac electrodes located external to the patient;
      circuitry, disposed within a housing of the external respiratory therapy device, configured to generate an electrocardiogram (ECG) signal based on the sensed cardiac electrical activity;
      a cardiac event detector configured to detect cardiac dysfunction events based on the ECG signal; and
      circuitry, disposed within the external respiratory therapy device housing, the circuitry configured to collect information based at least in part on the ECG signal, the collected information stored during each of multiple uses of the respiratory therapy device, the multiple uses corresponding to multiple sleep periods during which the patient uses the external respiratory therapy device; and
   a processor located external to the patient and configured to analyze cardiac conditions of the patient over the multiple uses based on the collected information.

2. The medical system of claim 1, wherein the cardiac event detector is configured to detect arrhythmia.

3. The medical system of claim 1, wherein the processor is configured to develop a trend of one or more cardiac conditions related to heart failure.

4. The medical system of claim 1, wherein the processor is configured to develop a trend of cardiac and respiratory conditions related to heart failure.

5. The medical system of claim 1, wherein the processor is configured to determine relationships between the cardiac dysfunction events and the respiratory events.

6. The medical system of claim 1, wherein the processor is configured to monitor progression of heart failure based on the collected information.

7. The medical system of claim 1, wherein the processor is configured to diagnose cardiac disorders and respiratory disorders based on the collected information.

8. The medical system of claim 1, wherein the ECG signals are not used to control the respiratory therapy.

9. The medical system of claim 1, wherein the ECG signals are used at least in part to adjust the respiratory therapy.

10. The medical system of claim 1, further comprising an implantable cardiac therapy device, wherein operation of the implantable cardiac therapy device is based at least in part on the ECG signal and the respiratory events.

11. The medical system of claim 10, wherein the implantable cardiac therapy device is configured to deliver an electrical cardiac therapy to treat heart failure and delivery of the electrical cardiac therapy is based at least in part on the ECG signal and the respiratory events.

12. The medical system of claim 1, further comprising an implantable cardiac therapy device, wherein operation of the implantable cardiac therapy device is based at least in part on the collected information.

13. The medical system of claim 12, wherein the implantable cardiac therapy device is configured to deliver an electrical cardiac therapy to treat heart failure and delivery of the electrical cardiac therapy is based at least in part on the ECG signal.

14. The medical system of claim 1, wherein the processor is further configured to determine heart rate variability based on the collected information.

15. The medical system of claim 1, wherein the external respiratory therapy device is configured to cause another device to initiate delivery of a cardiac therapy based on detection of arrhythmia by the processor.

16. The medical system of claim 1, wherein the control circuitry is configured to control delivery of the respiratory therapy based at least in part on the respiratory events and the cardiac conditions.

17. The medical system of claim 1, wherein the external respiratory therapy device comprises a mask assembly, the external respiratory therapy comprises positive airway pressure that is delivered through the mask assembly, the one or more cardiac electrodes are mechanically coupled to the mask assembly, and the mask assembly is configured to hold the one or more electrodes against the patient during delivery of the external respiratory therapy to facilitate sensing of the cardiac electrical activity.

18. A medical system, comprising:
   an external respiratory therapy device configured to deliver an external respiratory therapy to a patient, the external respiratory therapy device including:
      means for detecting respiratory events;
      means for controlling the external respiratory therapy based on the detected respiratory events;
      means for externally sensing cardiac electrical activity;
      means for generating an electrocardiogram (ECG) signal based on the sensed cardiac electrical activity;
      means for detecting cardiac dysfunction events based on the ECG signal;
      means for collecting and storing information based at least in part on the ECG signal, the information collected during multiple deliveries of the external respiratory therapy, the multiple deliveries corresponding to multiple sleep periods during which the patient uses the external respiratory therapy device; and
      means for externally analyzing cardiac conditions of the patient based on the information collected over the multiple deliveries of the external respiratory therapy.

* * * * *